Figure 1:
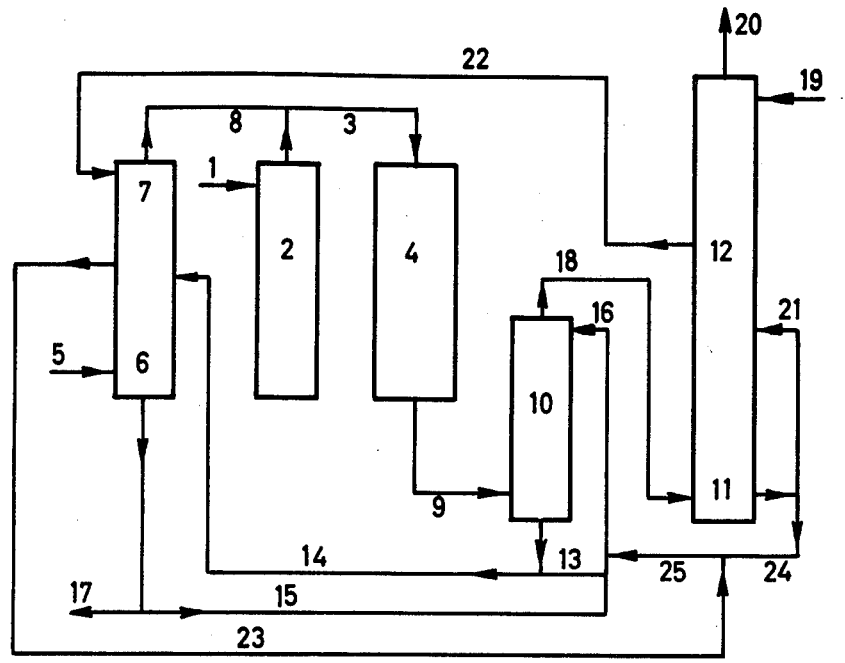

United States Patent [19]
Aicher et al.

[11] 4,119,673
[45] Oct. 10, 1978

[54] MANUFACTURE OF CONCENTRATED AQUEOUS SOLUTIONS OF FORMALDEHYDE

[75] Inventors: Albrecht Aicher, Frankenthal; Hans Haas, Ludwigshafen; Hans Diem, Ludwigshafen; Christian Dudeck, Ludwigshafen; Fritz Brunnmueller, Ludwigshafen; Gunter Lehmann, Ludwigshafen, all of Fed. Rep. of Germany

[73] Assignee: BASF Aktiengesellschaft, Ludwigshafen, Fed. Rep. of Germany

[21] Appl. No.: 613,925

[22] Filed: Sep. 16, 1975

[30] Foreign Application Priority Data

Sep. 18, 1974 [DE] Fed. Rep. of Germany ....... 2444586

[51] Int. Cl.² ............................................. C07C 45/16
[52] U.S. Cl. ................................. 260/603 C; 260/606
[58] Field of Search ............ 260/603 HF, 606, 603 C, 260/603 L

[56] References Cited
U.S. PATENT DOCUMENTS

| 2,436,287 | 2/1948 | Brondyke | 260/603 HF |
| 2,462,413 | 2/1949 | Meath | 260/603 HF |
| 3,728,398 | 4/1973 | Manx | 260/603 HF |
| 3,928,461 | 12/1975 | Diem et al. | 260/603 HF |

Primary Examiner—James O. Thomas, Jr.
Assistant Examiner—Werren B. Lone
Attorney, Agent, or Firm—Keil, Thompson & Shurtleff

[57] ABSTRACT

Formaldehyde is manufactured by oxidative dehydrogenation of methanol in the presence of a silver catalyst and of certain amounts of steam and formaldehyde, some formaldehyde and a part of the water being withdrawn from the reaction mixture and recycled. The formaldehyde manufactured by the process may be used as a disinfectant, tanning agent, reducing agent and starting material for the manufacture of synthetic resin, adhesives and plastics.

17 Claims, 3 Drawing Figures

MANUFACTURE OF CONCENTRATED AQUEOUS SOLUTIONS OF FORMALDEHYDE

The invention relates to a process for the manufacture of formaldehyde by oxidative dehydrogenation of methanol in the presence of a silver catalyst and of certain amounts of steam and formaldehyde, some formaldehyde and a part of the water being withdrawn from the reaction mixture and recycled.

In the industrial manufacture of formaldehyde from methanol by dehydrogenating oxidation with air over silver catalysts in the presence of steam, the formaldehyde is usually washed out of the reaction gases with water. The starting mixture in general contains methanol (calculated as 100% strength) and water in a ratio of from 0.1 to 1.8 moles of water per mole of methanol. This ratio is arrived at by vaporization of from 50 to 95 percent strength by weight aqueous methanol solutions. On absorptions of the reaction mixture, the steam produced by the reaction and the steam contained in the starting mixture are condensed. The solution of the formaldehyde gas is not homogeneous; instead, the formaldehyde combines with water to give methylene glycol and higher polyoxymethylene glycols (J. F. Walker, Formaldehyde, 3rd edition (Reinhold Publishing Corp., N.Y., p.54). This process can be represented in outline by the following equations:

$$CH_2O + H_2O \rightarrow HO-CH_2-OH$$

$$2 HO-CH_2-OH \rightarrow HO-(CH_2O)_2\cdot H + H_2O \text{ etc.}$$

A concentrated aqueous solution of formaldehyde can only be used for certain applications, since it can neither be stored, nor transported, for extended periods. The most usual concentration is of the order of magnitude of from 30 to 37% by weight, especially the latter figure, since this represents a solution of optimum concentration which proves stable over extended periods, without precipitation of paraformaldehyde. Such solutions are required for the manufacture of phenolic resins.

On the other hand, solutions of maximum concentration have advantages for other applications, e.g. to save transport costs, if the time for transport is relatively long and to save evaporation costs in subsequent processes, e.g. the manufacture of urea-formaldehyde condensation resins or the manufacture of butynediol by reaction with acetylene.

Hitherto, the only method of preparing aqueous formaldehyde solutions of almost 100% by weight concentration was to dissolve paraformaldehyde in water. It is a disadvantage of this method that it requires a starting formaldehyde of even lower water content than that which it is desired ultimately to obtain. This process is therefore uneconomical and industrially valueless. According to another method, formaldehyde is manufactured over a silver catalyst in the usual way but instead of the conventional starting mixture used in the vaporizer, which contains 60% by weight of methanol and 40% by weight of water, a substantially more concentrated mixture containing from 90 to 100% by weight of methanol is employed and the reaction is carried out at a lower catalyst temperature, with a lower conversion of methanol. This gives a gas which, whilst it still contains formaldehyde at a concentration corresponding to that from other processes, has part of the water replaced by methanol. This gas of higher methanol content is absorbed in water. The methanol is then distilled from these solutions, which contain, e.g., 40% by weight of formaldehyde, 18% by weight of methanol and 42% by weight of water, down to a methanol content of 1.2% by weight, so that a solution containing 48% by weight of formaldehyde, 1.2% by weight of methanol and 50.8% by weight of water remains. This process is uneconomical and unsatisfactory to operate, since it requires a subsequent distillation which demands energy, provision of cooling water and expenditure on equipment, and entails losses of formaldehyde.

Finally, dilute formaldehyde solutions can be concentrated by distillation (J. F. Walker, loc.cit. pp. 123 et seq.). In one embodement of the process, distillation is carried out at low temperatures under reduced pressure, under which conditions in the main water is distilled off, since at low temperatures the equilibrium $$CH_2O + H_2O \rightleftharpoons HO-CH_2-OH$$

lies predominantly toward methylene glycol. In a second embodiment, distillation is carried out at high temperatures under pressure. Under these conditions the equilibrium is predominantly toward monomeric formaldehyde, which, in this embodiment, is distilled off at the top. In each case, however, the distillation entails additional costs and causes losses of formaldehyde.

Belgian Pat. No. 683,130 discloses the manufacture of a concentrated aqueous formaldehyde solution by passing an anhydrous mixture of methanol and air over a silver catalyst in the presence of inert gases and absorbing the resulting formaldehyde in water. This process gives formaldehyde in yields of from 80 to 86% of theory. The off-gas obtained after isolating the formaldehyde is optionally recycled. The examples show a methanol content of at least 1.8% in the formaldehyde solutions obtained. In all the examples the reaction is carried out with small amounts of starting materials. Since no steam is introduced into the gaseous starting mixture for the reaction, the absorption process gives formaldehyde solutions of up to 60 percent strength by weight.

German Published Application No. 2,022,818 teaches that starting mixtures which contain off-gas and steam give good yields of the end product with lower methanol content, and give more highly concentrated formaldehyde solutions, if the off-gas which here again originates from the actual reaction, is purified by treatment with basic compounds and/or oxidizing agents before it is recycled.

If the process described in the above Belgian patent is carried out on a technical scale, e.g. with from 50 to 200 kg of methanol per hour, and in particular on an industrial scale, e.g. with from 0.2 to 20 metric tons of methanol per hour, the yield of formaldehyde is less than 88% of theory and 50 percent strength by weight formaldehyde solutions containing up to 2.25% of methanol are obtained.

Austrian Pat. No. 218,492 discloses purifying air by passing it through dust filters, then washing it with aqueous sodium hydroxide solution of from 5 to 10 percent strength by weight and subsequently washing it with methanol, potassium permanganate and water. The patent explains that this method of purification is involved, expensive and ineffective and teaches purifying air using aqueous formaldehyde solution of up to 30 percent strength by weight, produced in the formaldehyde plant, as the wash liquid. The example and description show that after the wash treatment the entire formaldehyde solution is directly processed further and is not recycled as wash liquid. The solutions produced contain 2.2% by weight of methanol and 0.005% by weight of formic acid. It is pointed out that the wash takes place at temperatures at which a minimum amount of formaldehyde is taken up by the air intended for the reaction and recycled to the process; it is stated that as a result the small amounts of formaldehyde entrained do not interfere with the catalytic reaction (page 2, lines 16–28). A wash temperature of 55° C is recommended.

In the manufacture of concentrated aqueous solutions of formaldehyde, particularly on an industrial scale, it is not a single aspect of the outcome of the process, e.g. the concentration of the solution, which is important.

It is an object of the present invention to provide a process which gives the highest possible concentration of formaldehyde solution, good yield, better space-time yield of end product, long catalyst life, and minimum content of methanol, and of formic acid formed in the reaction, even if crude methanol is used.

The present invention relates to a new process for achieving, more simply and more economically, improved overall results in respect of high concentration of the resulting formaldehyde solution, improved yield of end product, high conversion and low content of methanol and formic acid in the solution.

We have found that an advantageous manner of obtaining concentrated aqueous solutions of formaldehyde by oxidative dehydrogenation of methanol with air over a silver catalyst, in the presence of steam, at elevated temperatures, with subsequent absorption of the resulting formaldehyde in water, is to carry out the reaction with a throughput of from 1 to 3 metric tons of methanol per square meter of catalyst bed cross-section per hour, in the presence of from 0.1 to 1.8 moles of water and from 0.04 to 0.4 mole of formaldehyde per mole of total methanol fed to the catalyst, and to withdraw the formaldehyde and from 0.1 to 1.8 moles of water per mole of total methanol fed to the catalyst from the reaction mixture after the reaction and add it to the starting mixture.

Further, we have found that an advantageous method of carrying out the above process is to abstract a part of the formaldehyde and water from the formaldehyde solution, formed in the absorption stage, by means of the air fed to the reaction, at a temperature of from 60° to 90° C.

Further, we have found that it is advantageous to vaporize a part of the formaldehyde solution formed in the absorption stage and recycle it to the reaction.

Further, we have found that it is advantageous if, simultaneously, a part of the formaldehyde and water is abstracted from the formaldehyde solution, formed in the absorption stage, by means of the air fed to the reaction, at a temperature of from 60° to 90° C, and to vaporize a part of the formaldehyde solution, formed in the absorption stage, and recycle it to the reaction.

Further, we have found that it is advantageous to abstract from the reaction mixture, after the reaction, from 0.005 to 0.05 mole of methanol per mole of total methanol fed to the catalyst, and introduce it into the starting mixture.

Compared to conventional processes, the process of the invention — particularly on an industrial scale — is simpler and more economical and gives better overall results, i.e. high concentrations of the formaldehyde solution produced, better yield of end product, high conversion and low content of methanol and formic acid in the solution. In the new process, formaldehyde yields of from 89 to 91% of the theoretical yield are obtained in a single pass. The aqueous solutions obtained after absorption of the formaldehyde from the gases in which it is present contain from 50 to about 65% by weight, preferably from 50 to 55% by weight, of formaldehyde and have a methanol content of only from 0.8 to 2.0% by weight. The formic acid content of the formaldehyde solution obtained is low, as a rule less than 0.015% by weight, based on a 50 percent strength by weight formaldehyde solution. The process of the invention — particularly on an industrial scale — is less trouble-prone and gives a higher and more constant conversion of the starting mixture, longer catalyst life, and permits the use of a large catalyst bed cross-section. No special measures are needed to prevent temperature fluctuations in the catalyst. These advantageous results are achieved together with a longer catalyst life, and therefore fluctuations in the results obtained are avoided for extended periods. It is not necessary to use an additional inert gas. It is also not necessary to distil the formaldehyde solution. Because of the simplified procedure, less formaldehyde is entrained with the off-gas or waste water, and hence pollution of the atmosphere and of the waste water is reduced; accordingly, the process of the invention represents an advance over the art, from an environmental point of view. It is a special and surprising advantage of the process of the invention that more highly concentrated aqueous methanol solutions, especially of from 78 to 98% strength by weight, can be used and are preferred.

The results are also surprising in relation to the art. In the process disclosed in the above Austrian Patent (55° C, 30 percent strength by weight solution) the vapor pressure is 10 mm Hg. Since the temperature of a formaldehyde solution of 40 percent strength by weight, or more, is at least 50° C if the formation of polymers is to be avoided, the solution has a substantial vapor pressure. The vapor pressure of formaldehyde solutions increases greatly with increasing formaldehyde content and, for a 40 percent strength by weight solution, is 13.1 mm Hg at 55° C, whilst for a 50 percent strength by weight solution it is 17.0 mm Hg at 60° C and 55 mm Hg at 80° C. Formaldehyde is entrained with the air proportionately to this vapor pressure. It was to be expected that this would interfere with economical and simple operation of the process and lower the yield of end product, and that, in accordance with the teaching of J. Chem. Phys., 19 (1951), 176 et seq. and Recueil 58 (1939), 39 et seq., the entrained formaldehyde would be decomposed over the silver catalyst, to give carbon monoxide, methanol and other by-products. It was also to be expected that increased vaporization of formaldehyde would lead to deposits of paraformaldehyde.

Suitable starting materials for the process are pure methanol or technical-grade methanol, advantageously in the form of their mixture with water; the concentration of the aqueous mixtures can suitably be between 60 and 100% by weight, preferably between 70 and 100% by weight and especially from 78 to 90% by weight of methanol. In a preferred embodiment, aqueous solutions of from 78 to 85 percent by weight can be vaporized, and the recycled water and methanol, and the formaldehyde, can be added to these solutions in the vaporizer or to the stream of vapor produced from the solutions. For example, the recycled portion of the formaldehyde solution can be vaporized separately and the vapor can then be mixed with the methanol vapor and/or with the air. In another variant, the recycled part of the formaldehyde solution is combined with additional methanol and the mixture is vaporized. Analogous variants result from simultaneous or subsequent admixture of air. In all these embodiments, additional quantities of water, suitable as a mixture with methanol, may be used. The recycled part of the formaldehyde solution can also be added to the starting mixture in the vaporizer, or be fed into the additional water introduced, or be introduced, together with the methanol, into the vaporizer. In a preferred embodiment of the process, the recycled part of the formaldehyde solution is mixed with further methanol and water and the mixture is vaporized, whilst passing air through the liquid. In each case, the term "total methanol fed to the catalyst" is to be understood as the total mixture of starting methanol and recycled methanol.

Crude methanol, which as a rule is purified by the processes disclosed in German Printed Application No. 1,277,834, German Pat. No. 1,136,318 ang German Pat. No. 1,235,881, by separating off a lower-boiling fraction, and/or by treatment with oxidizing agents and/or alkalis, may also be used. The methanol vapor and steam can be generated separately and mixed with air, but it is advantageous to vaporize an appropriate aqueous solution of methanol and mix air with the vapor mixture; this is preferably done at the vaporization stage by passing the gas through the methanol solution. The air may be introduced above the vaporizer bottom or, preferably, into the latter.

The silver catalysts generally used for the manufacture of formaldehyde, e.g. those described in German Printed Application No. 1,231,229 and in Ullmanns Encyklopadie der technischen Chemie, volume 7, pp. 659 et seq., may be used for the process of the invention. Preferably, two-layer and multi-layer silver catalysts are used, e.g. the catalysts described in German Printed Application No. 1,294,360 and in German Printed Application 1,903,197. Regarding the manufacture of the catalyst and the method of carrying out the reaction with these catalysts, reference may be made to the above publications. In a preferred embodiment, the reaction is carried out with a total catalyst bed thickness of from 15 to 35 mm and 3 or more layers of silver crystals, a part of the layers containing from 72.5 to 89% by weight of the catalyst of particle size from 1 to 2.5 mm, a part of the layers containing from 2.5 to 7.5% by weight of the catalyst of particle size from 0.75 to 1 mm and the remaining part of the layers containing from 8.5 to 20% by weight of the catalyst of particle size from 0.2 to 0.75 mm. Preferred catalysts are those disclosed in German Printed Application No. 2,322,757. The diameter: thickness ratio of the catalyst bed, which preferably consists of two or more layers of different particle size, is at least 25, preferably from 40 to 200 and especially from 60 to 100. In general, the diameter is at least 500, preferably from 1,500 to 4,000 and especially from 1,700 to 3,000 mm.

The use of an inert gas is unnecessary and, at reaction temperatures of not less than 550° C and in particular of 600° C, is even inappropriate. If necessary, the catalyst can be heated by means of hot inert gases, suitably nitrogen or combustion gases of low carbon content, e.g. at a temperature of from 400 to 800° C. This embodiment is more advantageous than the use of indirect heating, e.g. electrical heating, particularly when using large amounts of catalyst in industrial operation.

Amounts of oxygen of from 0.15 to 0.60 mole, preferably from 0.15 to 0.50 mole, in the form of air, may be used per mole of methanol. The oxidation is also carried out by conventional methods, e.g. by passing a vapor/gas mixture of methanol vapor, air, inert gas if appropriate, steam and recycled formaldehyde vapor, in the above amounts, through the silver catalyst at from about 550° to 780° C, especially at from 650° to 720° C. It is desirable to cool the reaction gases leaving the catalyst zone quickly, e.g. in less than 0.2 second, suitably to from 50° to 300° C, advantageously to from 60° to 170° C and especially to from 130° to 160° C. The cooled gas mixture is then passed to the absorption stage. The stage of production of the formaldehyde is in general carried out at pressure of from 0.5 to 2 atmospheres, preferably from 1.1 to 1.8 atmospheres, either batchwise or, preferably, continuously.

The starting mixtures, which is in the vapor state, contains both freshly added water and methanol (feed mixture) and recycled water and, in most cases, recycled methanol. A throughput of from 1 to 3, preferably from 1.4 to 2.4, metric tons of methanol per square meter of catalyst bed cross-section per hour is used, with from 0.1 to 1.8, preferably from 0.5 to 1.5, moles of water and from 0.04 to 0.4, preferably from 0.05 to 0.2, mole of formaldehyde per mole of total methanol fed to the catalyst.

The recycled materials, namely water, formaldehyde and, if appropriate, methanol, can be taken from the reaction mixture between the catalyst bed and the absorption stage, but as a rule it is advantageous to abstract them from the aqueous formaldehyde solution formed in the absorption stage (the absorption solution) by separating off a part of this solution, or by extraction with a gas, suitably by treating the air fed to the reaction with the above absorption solution or, preferably, with a part thereof. Preferably, the reaction is first carried out with the feed mixture and air, and recycling in accordance with the process of the invention is only started after a certain amount of absorption solution has been produced, e.g. after from 1 to 72 hours in the case of a throughput of 2 metric tons of methanol per square meter of catalyst bed cross-section. The formaldehyde solution obtained in the absorption stage as a rule contains from 50 to 65, preferably from 50 to 55, percent by weight of formaldehyde, from 0.8 to 2, preferably from 1 to 1.7, percent by weight of methanol and from 0.005 to 0.015% by weight of formic acid.

In one of the above preferred embodiments, a part of the formaldehyde, water and, if appropriate, methanol, suitably from 0.04 to 0.4, preferably from 0.05 to 0.2, mole of formaldehyde, suitably from 0.1 to 1.8, preferably from 0.5 to 1.5, moles of water and suitably from 0.005 to 0.05, preferably from 0.008 to 0.03, mole of methanol per mole of total methanol fed to the catalyst (i.e. per mole of total methanol in the starting mixture before reaching the catalyst bed) is abstracted from the absorption solution by means of the reaction air, at from 60° to 90° C, preferably from 75° to 83° C, by washing the air with the absorption solution. Advantageously, from 10 to 25 times the amount of formaldehyde solution obtained per hour in the absorption stage is circulated as wash solution. The reaction air is washed using a ratio of from 300 to 5,000, preferably from 1,000 to 3,000, parts by volume of air per part by volume of wash solution. As a rule, the washing process is carried out in wash towers (wash columns); e.g., the wash liquid is charged in at the top of the column and the reaction air is suitably passed up through the column from the bottom, in counter-current. Wash columns which may be used are sieve tray columns, Oldershaw columns, glass tray columns, bubble-cap tray columns, valve tray columns, packed columns and columns with rotating inserts. It is advantageous to use tray columns wherein from 0.03 to 0.8 part by volume, per hour, of wash solution may be introduced per part by volume of the total space of the column. In bubble-cap tray columns the ratio of the weir height to the diameter is from 0.2 to 0.4; whilst in ball valve tray columns and sieve tray columns, hole diameters of from 5 to 15 mm, ball diameters of from 8 to 30 mm and tray spacings of from 300 to 800 mm are preferred. Suitably, from 30 to 80 metric tons of wash solution are introduced per hour per square meter of column cross-section, and a throughput of from 1 to 30 metric tons of air per hour per square meter of column cross-section is used. The temperature is preferably measured at the column top; the wash is carried out under atmospheric or superatmospheric pressure, batchwise or continuously, the latter being preferred as a rule. In this embodiment, the reaction air which has been washed as described above is preferably not passed into the bottom of the vaporizer but is introduced directly into the stream of vapor of the feed mixture, suitably above the liquid level of the freshly added aqueous methanol solution in the vaporizer.

In an advantageous method of this preferred embodiment, the absorption is carried out in several stages, e.g. in 2 to 4 absorption columns, which may be connected in series, and a part of the concentrated absorption solution from the 1st stage or column is withdrawn and used for the wash. A further part is taken from the dilute solution of a subsequent stage and used to treat the washed air in counter-current. This second part is preferably taken from the 3rd and/or 4th stage or column in the case of an absorption carried out in 4 or more stages, or from the 3rd stage in the case of a 3-stage absorption. Preferably, this second part of the formaldehyde solution contains from 1 to 10, preferably from 2 to 5, percent by weight of formaldehyde, from 87 to 98.5, preferably from 93 to 97.5, percent by weight of water and, if appropriate, from 0.1 to 3.0, preferably from 0.5 to 1.2, percent by weight of methanol and/or, if appropriate, from 0.0001 to 0.015% by weight of formic acid. This treatment is again suitably carried out by washing the air in the above manner under the stated washing conditions, e.g. as the second stage or second column, suitably of from 5 to 10 trays, of an appropriate washing installation. This is an advantageous method of recycling residual formaldehyde, water and methanol to the reaction.

The reaction may, e.g., be carried out by the following method A (FIG. 1): methanol and water are charged continuously through an inlet 1 into a vaporizer 2, vaporized and then fed via line 3 to the catalyst bed in a reactor 4. Air for the reaction enters a two-part wash column via line 5, is washed in the lower part 6 with concentrated formaldehyde solution and in the upper part 7 with dilute formaldehyde solution, and then enters the methanol/steam mixture in line 3 via the connecting line 8. After reaction in 4, the reaction mixture passes via the connecting line 9 into the first column 10 of a 3-stage 10, 11, 12 absorption installation comprising 2 absorption columns. A part of the formaldehyde solution formed in 10 is circulated, via connecting lines 13 and 14, the part 6 of the wash column and connecting lines 15 and 16, to serve as the solution for washing the air. The absorption column 10 has its own circulation of the absorption solution in 13 and 16. The concentrated formaldehyde solution is discharged continuously via line 17 and passed to its subsequent destination. The off-gas from 10 passes via the connecting line 18 into the 2nd absorption column, where it meets water, in counter-current, which is fed in via the line 19, and issues at the top 20 of the column. The dilute formaldehyde solution formed in 11 is circulated via the connecting line 21. A part of the dilute solution formed in 12 is abstracted and used as the solution for the 2nd air wash, for which it passes through the connecting line 22, the part 7 of the wash column and the discharge line 23. This circulation is connected to the 1st column via the connecting lines 24 and 25.

In all the embodiments, the absorption itself is advantageously carried out in 2 stages, suitably in the form of a wash of the off-gas. The mixture of reaction gas and steam is washed with an absorption mixture from the first stage, which preferably contains from 50 to 65% by weight of formaldehyde (calculated as 100% strength) and from 34.2 to 48% by weight of water and from 0.8 to 2.0% by weight of methanol, based on the absorption mixture, and an absorption mixture from the first column of the 2nd stage, which preferably contains from 30 to 42% by weight of formaldehyde (calculated as 100% strength) and from 53 to 69% by weight of water and from 1 to 5% by weight of methanol, based on the absorption mixture, as the absorption solution. As a rule, however, the off-gas is washed in absorption columns in the form of scrubbers or wash towers (wash columns); e.g., the wash liquid is introduced in the upper third, or advantageously at the top, of the columns, and the reaction mixture is passed in counter-current through the column, preferably upward from the column bottom. Wash columns or scrubbers which can be used are sieve tray columns, Oldershaw columns, glass tray columns, bubble-cap tray columns, valve-tray columns, trickle towers, spray towers, Feld scrubbers, Schroder scrubbers, packed columns and apparatuses with rotating inserts. It is advantageous to use tray columns which can handle the above hourly throughput of wash solution entering the column. In the case of ball valve tray columns and sieve tray columns, hole diameters of from 5 to 15 mm, ball diameters of from 8 to 30 mm and tray spacings of from 300 to 800 mm are preferred. A length ratio, or tray ratio, of the second absorption column to the first absorption column of from 1.5 to 3:1 is preferred. The throughputs of the mixtures are measured at their point of entry into the absorption column. A throughput, per hour per square meter of column cross-section, of from 2.5 to 5.0 metric tons of reaction mixture in the first stage and of from 1.5 to 4.0 metric tons of off-gas in the second stage, and/or a throughput, of absorption mixture per hour per square meter of column cross-section, of from 35 to 50 metric tons in the first stage and from 12 to 20 metric tons in the first column of the second stage, is preferred. The absorption is preferably carried out at from 55° to 90° C, especially from 55° to 85° C, in the first stage, and at from 40° to 65° C in the second stage (the temperatures being measured at the column top where columns are involved), under atmospheric or superatmospheric pressure and as a rule continuously.

Preferably, the aqueous solution which forms at the bottom of the two absorption columns by absorption of formaldehyde, from the cooled reaction mixture, in water is used as the wash liquid and is circulated via a cooling zone and the top of the column. Preferably, the wash liquid is mixed as uniformly and rapidly as possible with the reaction gas at the top of the column, e.g. by spraying it through nozzles or by using a perforated tray. Advantageously, sufficient water is introduced initially into both stages, and/or sufficient water is added hourly, that the above amounts of water are fed in at the column top in counter-current (to the reaction mixture) and the water forms solutions of the above compositions with the absorbed formaldehyde in the first and second stages. These amounts of water depend on the amount of water condensed from the reaction gas, the proportion of solution discharged at the column bottom and any proportions of water re-entrained by the reaction gas. Preferably, the amounts of formaldehyde solution discharged from the bottom of the first absorption stage is such as to maintain a constant liquid level in the bottom of the columns.

It is advantageous to use only one absorption column in the first absorption stage and more than one wash column or scrubber, preferably from 2 to 6, in the second stage of the absorption. In a preferred embodiment, the first stage is run with one column, under the above conditions. The gas issuing from the first column is then fed into the first column of the second stage, preferably directly into the liquid circulated from the bottom. Above, or next to, the second column there are the further columns belonging to the second stage, e.g. a 3rd and a 4th wash column. Preferably, these further columns also each comprise a circulation of the wash liquid as in column 2, preferably with a constant liquid level in the bottom, and with trickling or spraying devices or nozzles at the top of the column. Advantageously, an aappropriate part of the liquid is fed to the liquid circulation of the preceding column. For example, a part of the circulating liquid from column 4 is fed to the circulation of column 3, at the top of the latter, and at the same time a part which is fed in the same way to column 2 or 1 is taken continuously from the bottom of columns 3 and 2 respectively. The throughput in the subsequent columns, e.g. the 3rd and 4th columns, corresponds to those in the preceding column, in the instance of 2nd column (1st column of the 2nd stage). In the 3rd and 4th columns, temperatures of from 20 to 65° C are generally employed. In the case of a 4-column absorption with 3 columns in the 2nd stage, it is advantageous to produce, for use as wash liquids, solutions containing from 1 to 30% by weight of formaldehyde (calculated as 100% strength) in the 3rd column and containing from 0.1 to 8% by weight of formaldehyde in the 4th column, suitably by addition of water, in particular at the top of the last column. The off-gas which issues from the last column retains only a little formaldehyde, mostly less than 0.1% by weight, and about 1.5% by weight of hydrogen, based on the total off-gas. The off-gas is combustible and the remainder of the formaldehyde is thus combusted without polluting the environment. As regards the total length or number of plates of all the columns of the 2nd stage, it is advantageous if the ratio of the length, or number of plates, of the 2nd, or of the 2nd and 3rd columns combined, of the 2nd stage, to the first column of the 2nd stage, is from 1 to 2:1. Total length means the length of the total space in which the wash and absorption take place. The first absorption stage may, e.g., comprise a length of from 2 to 8 m, preferably from 4 to 6 m, and the 2nd stage a total length of from 8.8 to 16 m.

In a further preferred embodiment, a part of the formaldehyde solution formed during the absorption, advantageously the more dilute solution from the 2nd absorption stage, is vaporized and recycled to the reaction. A portion of formaldehyde, water and, if appropriate, methanol, suitably from 0.04 to 0.4, preferably from 0.05 to 0.2, mole of formaldehyde, suitably from 0.1 to 1.8, preferably from 0.5 to 1.5, moles of water and suitably from 0.005 to 0.05, preferably from 0.008 to 0.03, mole, of methanol per mole of total methanol fed to the catalyst (i.e. per mole of total methanol in the starting mixture before reaching the catalyst bed) is abstracted from the absorption solution. Preferably, the absorption is carried out in the above 2-stage installation with 2 or 3 columns in the 2nd stage. An embodiment which uses one column in the 1st absorption stage and 3 columns or 3 column sections in the 2nd absorption is preferred; in this, a part of the solution is taken from the bottom or lowest tray of the penultimate (3rd) column, and the remainder of the solution is fed to the top of the 2nd column and water is introduced at the top of the 4th column. The last column is suitably a tray column, preferably with 10 trays, in which the absorption solution is at from 20° to 65° C. The formaldehyde solution can be taken from only one column bottom, suitably the bottom of the penultimate column, or preferably from several columns, suitably the bottom of the last (4th) and/or the penultimate (3rd) column of the 2nd absorption stage. The throughput of off-gas and the amount of water added are adjusted so that, preferably, an aqueous formaldehyde solution containing from 6 to 28, preferably from 12 to 23, percent by weight of formaldehyde, from 1 to 5, preferably from 2 to 4, percent by weight of methanol and/or from 0.0001 to 0.015% by weight of formic acid is taken off and recycled, e.g. to the vaporizer or to a separate 2nd vaporizer. The 2nd vaporizer serves only to vaporize the solution taken off and is generally operated under the same conditions as the abovementioned methanol vaporizer. Advantageously, both vaporizations are carried out in a single column with 2 separate vaporization points. A suitable ratio is from 0.04 to 0.4, preferably from 0.05 to 0.2, mole of formaldehyde recycled from the last (3rd) column, from 0.1 to 1.8, preferably from 0.5 to 1.5, moles of water recycled from the penultimate (3rd) column and from 0.005 to 0.05, preferably from 0.008 to 0.03, mole of methanol recycled from the penultimate (3rd) column per mole of total methanol fed to the catalyst (total methanol in the starting mixture before reaching the catalyst bed), the formaldehyde advantageously originating entirely from the proportion taken off the penultimate (3rd) column.

Figure 2:
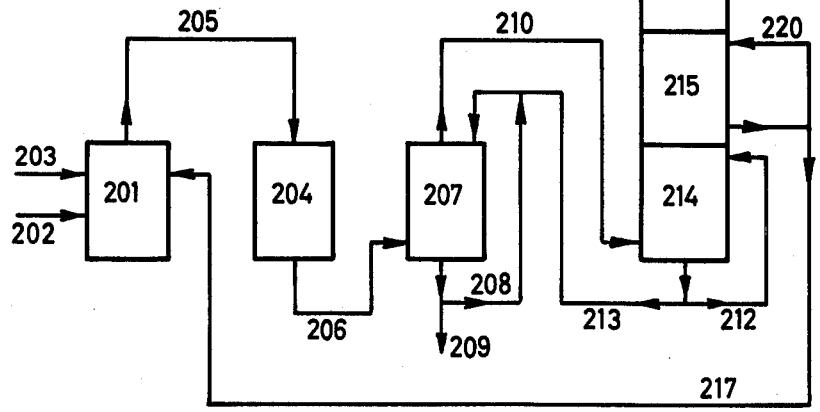

By way of example, this preferred embodiment can be carried out by method B (FIG. 2): a freshly introduced aqueous methanol solution 203 is vaporized in a two-part vaporizer 201 whilst passing in air 202 and the vapor mixture is passed through the connecting line 205 and reacted in the reactor 204. The reaction mixture is passed through the line 206 into the 1st absorption stage (absorption column 207), where the formaldehyde solution formed serves as the wash liquid and is circulated via the connecting line 208. The concentrated formaldehyde solution is taken off via the discharge line 209 and processed further. The off-gas enters the 2nd absorption stage, a three-part absorption column 214, 215, 216 via the connecting line 210. In the lower part 214, the absorption solution formed is circulated in the circuit 212 and a part of the solution is passed to the 1st stage via the return line 213. In the middle part 215, the absorption solution formed is circulated circuit 220. In the upper part 216 of the column, water is fed in at the top 219 and the off-gas is discharged via the outlet 218. Formaldehyde solution is continuously taken off the bottom of the middle part 215 of the column and recycled via the connecting line 217 to the vaporizer 201.

Figure 3:
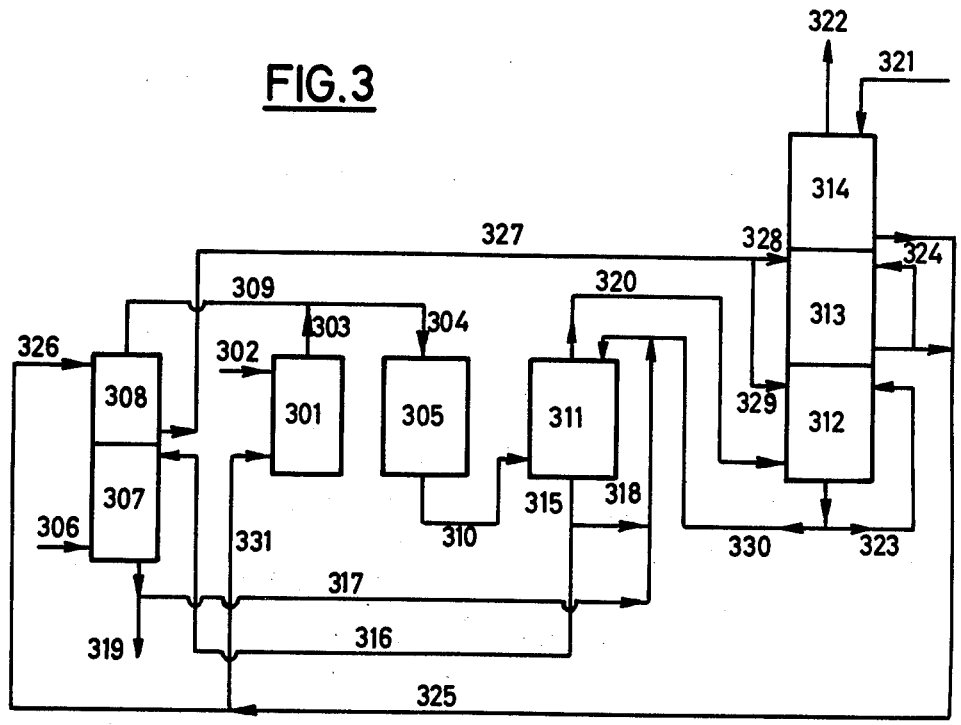

In a further preferred embodiment, the two above preferred embodiments are combined and the process is carried out by recycling a part of the absorption solution and using a further part for washing the reaction air. The combined process is advantageously carried out under the preferred conditions of the two embodiments. For example, the reaction is carried out by method C (FIG. 3): a freshly introduced aqueous methanol solution 302 is vaporized in a two-part vaporizer 301 and the vapor mixture is passed via the line 303 and the line 304 into the reactor 305. The reaction air enters a two-part wash column via the feed line 306, is washed with concentrated formaldehyde solution in the lower part 307 and with dilute formaldehyde solution in the upper part 308 and then enters the line 304 via the connecting line 309. After the reaction in the reactor 305, the reaction mixture passes via the connecting line 310 into the first column 311 of a 4-stage 311, 312, 313, 314 absorption installation comprising two absorption columns. A part of the formaldehyde solution formed in 311 is circulated via the connecting lines 315 and 316, the part 307 of the wash column and the connecting lines 317 and 318 to serve as the wash liquid for the air. The absorption column 311 has its own circulation of the absorption solution via 315 and 318. The concentrated formaldehyde solution is taken off via the line 319 and is processed further as required. The off-gas from 311 passes via the connecting line 320 into the second absorption column, where it encounters water fed in via the feed line 321 in counter-current, and issues at the top 322 of the column.

The dilute formaldehyde solution formed in 312 is circulated via the connecting line 323; the dilute formaldehyde solution formed in 313 is circulated via the connecting line 324. A proportion of the dilute solution formed in 313 and/or 314 is taken off and is used as the wash solution for the second air wash, being passed via the connecting lines 325 and 326, the wash column section 308 and the discharge line 327. This circulation is connected to stages 313 and/or 312 via the connecting lines 328 and/or 329.

A proportion of the dilute formaldehyde solution formed in 312, 313 and 314 is passed via line 330 to the top of the column 311. A further proportion of the dilute formaldehyde solution flowing through line 325 is passed via line 331 into the two-part vaporizer 301 and is also vaporized.

The formaldehyde which can be manufactured by the process of the invention is a disinfectant, tanning agent, reducing agent and valuable starting material for the manufacture of synthetic resins, adhesives and plastics. Regarding its uses, reference may be made to Ullmann, loc. cit., p. 670.

In the Examples which follow, parts are by weight. They bear the same relation to parts by volume as does the kilogram to the cubic meter.

EXAMPLE 1

An installation comprising a methanol vaporizer and a vertical reactor, as described for the above method A (FIG. 1) is used. At its top, the reactor has the inlet for the starting mixture, which is in the vapor state, and the reactor cover. The catalyst bed is below the reactor top and below it, in turn, is a cooling zone. The reactor is connected to an absorption installation.

187 parts of a catalyst of silver crystals, of the following composition, are introduced into the reactor:

| Proportion in the catalyst (% by weight) | | Particle size mm | | |
|---|---|---|---|---|
| Layer 1 | 12.9 | 0.4 | - | 0.75 |
| Layer 2 | 1.2 | 0.2 | - | 0.4 |
| Layer 3 | 5.3 | 0.75 | - | 1 |
| Layer 4 | 14.1 | 1 | - | 1.75 |
| Layer 5 | 66.5 | 1 | - | 2.5 |

Layer 2 is sprinkled onto layer 3 to form an annular layer in the edge zone. The diameter of the catalyst (bed) is 170 cm and the internal diameter of the annular layer is 167 cm. Per hour, a mixture of 4,630 parts of crude methanol and 945 parts of water is fed to the vaporizer and vaporized therein at 92° C and 1.3 atmospheres gauge. Per hour, 5,060.8 parts of formaldehyde, 232.6 parts of methanol, 1.1 parts of formic acid and 5.780.6 parts of water, from the 1st absorption column, are introduced continuously into the circulation of the wash liquid for the lower part of the wash column. From the upper part of the 2nd absorption column, 1,158 parts of aqueous formaldehyde solution (3.6% by weight of formaldehyde, 0.7% by weight of methanol and 0.005% by weight of formic acid) per hour are taken off continuously to act as the wash liquid for the 2nd air wash and are circulated by pumping, being introduced at the top of the wash column. 7,560 parts of formaldehyde solution per hour are taken off the wash column as the end product. The 1st and 2nd wash liquids are passed downward, and 8,368 parts of reaction air per hour are passed upward, in counter-current, at 81° C (at the column top) and 1.4 atmospheres. The air which leaves the wash column entrains, per hour, 602 parts of formaldehyde, 2.191 parts of water and 84 parts of methanol vapor. The air which has been washed in this way is mixed with the vapor mixture of methanol and water from the vaporizer, and the mixture is passed over the catalyst bed of finely divided silver at 690° C and 1.3 atmospheres total pressure, using a throughput of 2.04 metric tons of methaol per m$^2$ of catalyst bed cross-section per hour; the mixture is then cooled to 150° C and fed to the 1st absorption column. The off-gas is introduced into the bottom of the 2nd absorption column, in counter-current to 1,134 parts of water per hour entering at the top of the column, and then leaves the absorption installation. The solution for the 1st air wash is taken from the 1st absorption column and the solution for the 2nd air wash is taken from the upper part (3rd stage) of the 2nd column, and these solutions are circulated.

The throughput is 2.04 metric tons of methanol per square meter of catalyst bed cross-section per hour. 3,811 parts of formaldehyde (calculated a 100% strength) per hour are obtained in the form of a 50.4 per cent strength by weight aqueous solution containing 1.7% by weight of methanol and 0.008% by weight of formic acid. This corresponds to a yield of 90.3% of theory and a conversion of 97.1%. No cracks are observed in the catalyst bed. The yield of end product, the conversion and the methanol content and formic acid content of the formaldehyde solution obtained do not change for 120 days.

EXAMPLE 2

An installation comprising a methanol vaporizer and a vertical reactor, as illustrated for the above method B (FIG. 2) is used. At its top, the reactor has the inlet for the starting mixture, which is in the vapor state, and the reactor cover. The catalyst bed is below the reactor top and below it, in turn, is a cooling zone. The reactor is connected to an absorption installation. 187 parts of a catalyst of silver crystals, of the following composition, are introduced into the reactor:

| | Proportion in the catalyst (% by weight) | Particle size mm | |
|---|---|---|---|
| Layer 1 | 12.9 | 0.4 | - 0.75 |
| Layer 2 | 1.2 | 0.2 | - 0.4 |
| Layer 3 | 5.3 | 0.75 | - 1 |
| Layer 4 | 14.1 | 1 | - 1.75 |
| Layer 5 | 66.5 | 1 | - 2.5 |

Layer 2 is sprinkled onto layer 3 to form an annular layer in the edge zone. The diameter of the catalyst (bed) is 170 cm and the internal diameter of the annular layer is 167 cm. The reactor is connected to the 1st absorption column via a cooling zone. Per hour, a mixture of 4.5 parts of methanol, 1.12 parts of water and 8.05 parts of air is fed to the vaporizer, and vaporized at 67° C and 1.3 atmospheres. The starting mixture is passed through the catalyst bed (0.187 part) and is reacted at 700° C and 1.3 atmospheres. It is then cooled to 140° C. The reaction gas is now passed through the 1st absorption column, which is 5 meters long (1st stage) and then through the 2nd absorption stage (columns 2, 3 and 4). Column 2 is 4 meters long and columns 3 and 4 are together 9 meters long. Columns 1 to 4 are connected to one another and their wash liquids are each circulated. The absorption temperatures (measured at the top of the columns) are 75° C in column 1, 58° C in column 2, 42° C in column 3 and 40° C in column 4. The throughput of reaction mixture (measured at the column inlet) is 4.1 tonnes per hour per square meter of column cross-section in the 1st column (1st stage); the throughput of off-gas, in tonnes per hour per square meter of column cross-section, is 3.3 in the 2nd column (2nd stage), 3.2 in the 3rd column and 2.4 in the 4th column. Columns 1, 2 and 3 are packed columns and column 4 is a bubble-cap tray column.

The absorption mixtures contain: In the 3rd column, 18.0% by weight of formaldehyde, 79% by weight of water and 3% by weight of methanol. In the 4th column, 4.4% by weight of formaldehyde, 93.2% by weight of water and 2.4% by weight of methanol.

Per hour, 1.65 parts of formaldehyde solution are taken from the bottom of the 3rd column and 0.31 part of formaldehyde solution is taken from the bottom of the 4th column, and recycled to the vaporizer. Per hour, 1.08 parts of water are added to the circulation in the 4th column.

The throughput is 2.01 metric tons of methanol per square meter of catalyst bed cross-section per hour. A part of the end product, in the form of a concentrated formaldehyde solution, is continuously taken from the bottom of the 1st column. Per hour, 3.71 parts of formaldehyde (calculated as 100% strength) are obtained in the form of a 50.0 per cent strength by weight aqueous solution containing 1.5% by weight of methanol and 0.008% by weight of formic acid. This corresponds to a yield of 91.2% of theory and a conversion of 96.5%. The yield of end product and the methanol content and formic acid content of the formaldehyde solution produced remain constant for 120 days. No cracks are observed in the catalyst bed.

EXAMPLE 3

An installation comprising a methanol vaporizer and a vertical reactor, as illustrated for the above method C (FIG. 3) is used. At its top, the reactor has the inlet for the starting mixture, which is in the vapor state, and the reactor cover. The catalyst bed is below the reactor top and below it, in turn, is a cooling zone. The reactor is connected to an absorption installation. The same catalyst as in Example 2 is introduced into the reactor. The reactor is connected to the 1st absorption column via a cooling zone. Per hour, 4,500 parts of methanol are fed to the vaporizer and vaporized at 66° C and 1.3 atmospheres. Per hour, 37,354.6 parts of formaldehyde, 755.9 parts of methanol, 6.3 parts of formic acid and 24,875.7 parts of water from the 1st absorption column are continuously circulated as the wash liquid for the lower part of the wash column. 298.8 parts of aqueous formaldehyde solution (containing 5.0% by weight of formaldehyde, 2.5% by weight of methanol and 0.01% by weight of formic acid) per hour, taken from the bottom of the 4th absorption column, are continuously fed into the upper part of the wash column to act as the wash liquid for the 2nd air wash. 8,103.7 parts of air are introduced in counter-current to the 1st and 2nd wash liquids, at 77° C and 1.4 atmospheres. The air leaving the wash column entrains, per hour, 295 parts of formaldehyde, 82.2 parts of methanol and 1,131.5 parts of water as vapor. After leaving the wash column, 6,158.1 parts of an aqueous formaldehyde solution (60.6% by weight of formaldehyde, 1.1% by weight of methanol and 0.008% by weight of formic acid) are taken as end product from the 1st wash liquid. The remainder is fed into absorption column 1. The 2nd wash liquid is fed to the top of the 2nd absorption column.

The air washed in this way is mixed with the vapor mixture of methanol and water from the vaporizer and the mixture is passed over the catalyst bed of finely divided silver at 700° C and 1.3 atmospheres total pressure, at a throughput of 2.04 metric tons of methanol per square meter of catalyst bed cross-section per hour, and is then cooled to 150° C. The reaction gas in the vapor state is now passed through the 1st absorption column, of 5 m length (1st stage), and then through the 2nd absorption column (columns 2, 3 and 4). Column 2 is 4 meters long and columns 3 and 4 together are 9 meters long. Columns 1 to 4 are connected together and their wash liquids are each circulated. The absorption temperatures (measured at the column top) are 78° C in the 1st column, 60° C in the 2nd column, 44° C in the 3rd column and 40° C in the 4th column. The throughput of reaction mixture (measured at the column inlet) is 4.1 metric tons per hour per square meter of column cross-section in the 1st column (1st stage) and the throughput of off-gas, in metric tons per hour per square meter of column cross-section, is 3.3 in the 2nd column (2nd stage), 3.2 in the 3rd column and 2.4 in the 4th column. Columns, 1, 2 and 3 are packed columns and column 4 is a bubble-cap tray column. The absorption mixtures contain: In the 3rd column, 15.8% by weight of formaldehyde, 81.3% by weight of water and 2.9% by weight of methanol. In the 4th column, 5.0% by weight of formaldehyde, 92.5% by weight of water and 2.5% by weight of methanol.

Per hour, 1,975.5 parts of formaldehyde solution (56 parts of methanol, 313.7 parts of formaldehyde and 1,605.8 parts of water) are taken from the bottom of the 3rd column and recycled to the vaporizer. Per hour, 911.2 parts of water are added to the circulation of the 4th column.

The throughput is 2.04 metric tons of methanol per square meter of catalyst bed cross-section per hour. By taking off 6,158.1 parts of an aqueous formaldehyde solution from the 1st wash liquid, a yield of 89.9% of theory and a conversion of 98.5% are obtained. The yield of end product and the methanol content and formic acid content of the formaldehyde solution produced remain constant for 120 days. No cracks are observed in the catalyst bed.

We claim:

1. In a process for the manufacture of a concentrated aqueous solution of formaldehyde by a catalytic oxidative dehydrogenation reaction of a starting reaction mixture comprising water, methanol and air over a catalyst bed of silver crystals arranged in a reactor and in the presence of steam at elevated temperatures of about 550° C. to 780° C., followed by absorption in water of the formaldehyde formed, the improvement which comprises:
   carrying out the reaction with a throughput of said starting mixture consisting essentially of from 1 to 3 tonnes of methanol per square meter of catalyst bed cross-section per hour together with from 0.1 to 1.8 moles of water and 0.04 to 0.4 mole of formaldehyde per mole of total methanol fed to the catalyst;
   absorbing the formaldehyde in an absorption stage by washing the off-gas from the reactor with water to form an aqueous formaldehyde solution; and
   recycling part of the formaldehyde and water formed in the absorption stage, so as to return amounts of from 0.04 to 0.4 mole of formaldehyde and up to 1.8 moles of water per mole of total methanol fed to the catalyst, as an addition in making up said starting mixture.

2. A process as claimed in claim 1, wherein the returned amounts of formaldehyde and water are abstracted from said aqueous formaldehyde solution, formed in the absorption stage, by means of washing the air fed to the reaction with said solution at from 60° to 90° C.

3. A process as claimed in claim 1, wherein a part of the formaldehyde and water from said aqueous formaldehyde solution, formed in the absorption stage, is vaporized and recycled to the reaction for the return of said amounts of formaldehyde and water as an addition in making up said starting mixture.

4. A process as claimed in claim 1, wherein simultaneously one part of the returned amounts of formaldehyde and water is abstracted from said aqueous formaldehyde solution, formed in the absorption stage, by means of washing the air fed to the reaction with said solution at from 60° to 90° C., and another part of the returned amounts of formaldehyde and water is abstracted by vaporization from said aqueous formaldehyde solution, formed in the absorption stage, and recycled to the reaction, each of the abstracted parts of formaldehyde and water being joined together as said addition in making up said starting mixture.

5. A process as claimed in claim 1, wherein, after the reaction, from 0.005 to 0.05 mole of methanol per mole of total methanol fed to the catalyst is taken from the reaction mixture, and returned as an addition in making up said starting mixture.

6. A process as claimed in claim 1, wherein the reaction is carried out with a crude methanol feed.

7. A process as claimed in claim 1, wherein the reaction is carried out at from 550° to 780° C.

8. A process as claimed in claim 1, wherein the reaction is carried out at from 650° to 720° C.

9. A process as claimed in claim 1, wherein the reaction is carried out with a throughput of from 1.4 to 2.4 tonnes of methanol per square meter of catalyst bed cross-section per hour, and using from 0.5 to 1.5 moles of water and from 0.05 to 0.2 mole of formaldehyde per mole of total methanol fed to the catalyst.

10. A process as claimed in claim 1, wherein at least part of the returned amounts of formaldehyde and water is abstracted from said aqueous formaldehyde solution, formed in the absorption stage, by means of washing the air fed to the reaction with said solution at from 60° to 90° C.

11. A process as claimed in claim 10, wherein from 10 to 25 times the amount of said aqueous formaldehyde solution, formed in the absorption stage, is circulated per hour as wash solution and the air fed to the reaction is washed using a ratio of from 300 to 5,000 parts by volume of air per part by volume of wash solution.

12. A process as claimed in claim 10, wherein the wash solution is fed in at the top of a wash column and the reaction air is passed upwardly from the bottom through said wash column, in counter-current flow, the wash solution being fed into the wash column at from 30 to 80 tonnes per hour per square meter of wash column cross-section and the air throughput in said wash column being from 1 to 30 tonnes of air per hour per square meter of column cross-section.

13. A process as claimed in claim 2, wherein the absorption is carried out in 2 absorption stages with a total of from 2 to 7 absorption columns connected in series, one recycle stream of a concentrated formaldehyde solution being taken from the 1st absorption stage to wash said air fed to the reaction, and a further recycle stream of a dilute formaldehyde solution being taken from the 2nd absorption stage to also wash said air fed to the reaction, said absorption solutions being used to wash the air in counter-current, the further recycle stream being taken from at least one of the 3rd and 4th columns in the case of an absorption in 4 or more columns, or being taken from the 3rd column in the case of an absorption in 3 columns, and the formaldehyde solution of said further recycle stream having a concentration of from 1 to 10% by weight of formaldehyde and from 87 to 98.5% by weight of water.

14. A process as claimed in claim 3 wherein:
   the absorption is carried out in 2 absorption stages with a total of from 2 to 7 absorption columns connected in series, said aqueous formaldehyde solution being formed in said stages by washing the reaction gas/vapor mixture
   (a) in the first absorption stage with an absorption mixture containing from 50 to 65% by weight of formaldehyde, from 34.2 to 48% by weight of water and from 0.8 to 2.0% by weight of methanol, and
   (b) in the 1st column of the second stage with an absorption mixture containing from 30 to 42% by weight of formaldehyde, from 53 to 69% by weight of water and from 1 to 5% by weight of methanol;

the reaction gas/vapor mixture throughput in the first absorption stage is from 2.5 to 5.0 tonnes per hour per square meter of column cross-section while the reaction gas/vapor mixture throughput in the 1st column of the second absorption stage is from 1.5 to 4.0 tonnes per hour per square meter of columm cross-section;

the absorption liquid throughput in the first absorption stage is from 35 to 50 tonnes per hour per square meter of column cross-section while the absorption liquid throughput in the 1st column of the second stage is from 12 to 20 tonnes per hour per square meter of column cross-section; and the absorption is carried out at from 55° to 90° C in the first absorption stage and at from 40° to 65° C in the second absorption stage.

15. A process as claimed in claim 1, wherein:

the absorption is carried out in 2 absorption stages having one column in the first stage and three columns in the second stage, a bottom absorption liquid being at least partly returned in each column back to the top thereof as a circulated wash liquid;

the gas leaving the one column of the first stage is fed directly into the 1st column of the second stage, countercurrent to the circulating bottom liquid;

a part of the circulating liquid from the 4th column is fed into the wash liquid circulation at the top of the 3rd column;

at the same time, a part of the circulating liquid from the bottom of the 3rd column is fed into the wash liquid circulation at the top of the 2nd column; and the wash liquids in the 3rd and 4th columns are adjusted, by the addition of water, to correspond to an aqueous solution containing from 1 to 30% by weight of formaldehyde in the 3rd column and from 0.1 to 8% by weight of formaldehyde in the 4th column.

16. A process as claimed in claim 15, wherein the ratio of the lengths or numbers of plates of the 2nd and 3rd columns combined to that of the 1st column of the second stage is from 1 to 2:1, the length of the first absorption stage is from 2 to 8 m and the total length of the second stage is from 8.8 to 16 m.

17. A process as claimed in claim 15, wherein the formaldehyde solution being recycled as an addition in making up said starting mixture is taken from the bottom of at least one of the last or penultimate columns of the second absorption stage, and the throughput of reaction gas/vapor mixture and an addition of water being so chosen that an aqueous formaldehyde solution containing from 6 to 28% by weight of formaldehyde is taken off and recycled.

* * * * *